United States Patent [19]

Terao et al.

[11] Patent Number: 5,012,015

[45] Date of Patent: Apr. 30, 1991

[54] PROCESS FOR PRODUCING 2,4-DICHLORO-3-ALKYL-6-NITROPHENOL

[75] Inventors: Masanobu Terao, Hyogo; Yuzo Maegawa; Yasuyoshi Ueda, both of Osaka; Kiyoyasu Hashimoto, Nara; Takashi Omura, Hyogo, all of Japan

[73] Assignees: Daiei Chemical Co., Ltd., Hyogo; Sumitomo Chemical Co., Ltd., Osaka, both of Japan

[21] Appl. No.: 319,718

[22] Filed: Mar. 7, 1989

[30] Foreign Application Priority Data

Mar. 9, 1988 [JP] Japan ............................ 63-55593
Apr. 5, 1988 [JP] Japan ............................ 63-84347
Apr. 5, 1988 [JP] Japan ............................ 63-84348

[51] Int. Cl.$^5$ ................. C07C 205/26; C07C 205/20
[52] U.S. Cl. ................................. 568/709; 568/713
[58] Field of Search ........................... 568/709, 713

[56] References Cited

U.S. PATENT DOCUMENTS

| | | | |
|---|---|---|---|
| 3,903,178 | 9/1975 | Nakamura et al. | 568/709 |
| 3,928,470 | 12/1975 | Soula et al. | 568/709 |
| 4,038,328 | 7/1977 | Pelster | 568/709 |

FOREIGN PATENT DOCUMENTS

| | | | |
|---|---|---|---|
| 34326 | 11/1972 | Japan . | |
| 59122 | 5/1977 | Japan | 568/709 |
| 0073742 | 6/1979 | Japan | 568/709 |
| 57536 | 8/1984 | Japan | 568/709 |
| 60634 | 8/1984 | Japan | 568/709 |
| 1057536 | 3/1986 | Japan | 568/709 |
| 44552 | 2/1988 | Japan | 568/709 |

*Primary Examiner*—Werren B. Lone
*Attorney, Agent, or Firm*—Antonelli, Terry, Stout & Kraus

[57] ABSTRACT

2,4-Dichloro-3-alkyl-6-nitrophenol, which is a precursor of 2,4-dichloro-3-alkyl-6-aminophenol useful for the production of a cyan coupler to be used with a sensitive material in the field of a photography in color, is industrially advantageously produced by (a) nitration of 2,4,5-trichloro-3-alkylbenzene, followed by hydrolysis of the resulting 2,4,5-trichloro-3-alkyl-6-nitrobenzene, or (b) hydrolysis of 2,4,5-trichloro-3-alkylbenzene-6-sulfonic acid or a salt thereof, followed by nitration of the resulting 2,4-dichloro-3-alkylphenol-6-sulfonic acid or a salt thereof, the starting material usable for these processes being 4-alkylbenzenesulfonic acid or a salt thereof, which is easily available.

10 Claims, No Drawings

PROCESS FOR PRODUCING 2,4-DICHLORO-3-ALKYL-6-NITROPHENOL

The present invention relates to a process for producing an intermediate of a cyan coupler in the field of a photography in color. More specifically, the present invention relates to a process for producing a 2,4-dichloro-3-alkyl-6-nitrophenol which is a precursor of a 2,4-dichloro-3-alkyl-6-aminophenol useful for the production of a cyan coupler to be used with a sensitive material in such field.

Published Unexamined Japanese Patent Applications No. 47-34326 and No. 61-57536 disclose a process for producing the 2,4-dichloro-3-alkyl-6-nitrophenol, which comprises subjecting a 4-chloro-3-alkylphenol to sulfonation, followed by chlorination and successive nitration.

In order to obtain the desired compound of a high purity with a high yield, Published Unexamined Japanese Patent Application No. 61-60634 proposes chlorination of a 1-alkyl-4-nitrobenzene, followed by hydrolysis.

However, these known methods cannot be carried out industrially without problems to be solved. For example, in the former using the 4-chloro-3-alkylphenol as the starting material, it is difficult to prepare the starting material, because a m-alkylphenol such as m-ethylphenol and the 4-chloro-3-alkylphenol which is produced from the m-alkylphenol can hardly be obtained in a high purity. In the latter using the 1-alkyl-4nitrobenzene as the starting material, it can be prepared in a conventional manner comprising nitration of an alkylbenzene in a mixed acid. However, the product obtained is a mixture of ortho- and para-isomers, so that the product be purified to obtain the paraisomer in a high purity, resulting in decrease of a production yield.

The present inventors have undertaken extensive studies to solve the problems described above and find an industrially advantageous process for the production of 2,4-dichloro-3-alkyl-6-nitrophenol, and as a result, found a novel process for the production thereof, which can accomplish the object.

The present invention provides a process for producing a 2,4-dichloro-3-alkyl-6-nitrophenol represented by the following formula (I),

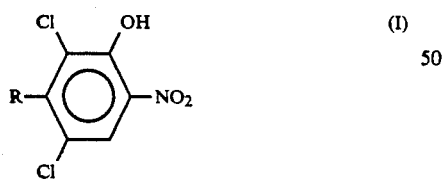

wherein R is a straight or branched alkyl group having 1 to 8 carbon atoms, which comprises (a) steps of subjecting a trichlorobenzene represented by the following formula (III),

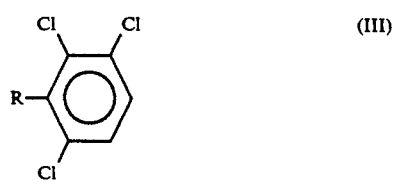

wherein R is as defined above, to nitration, and subjecting the resulting nitro-trichlorobenzene represented by the following formula (II),

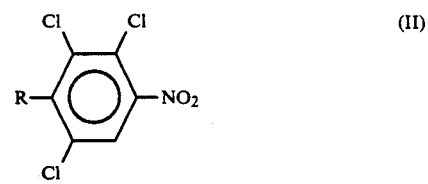

wherein R is as defined above, to hydrolysis, or (b) steps of subjecting a trichlorobenzenesulfonic acid, or a salt thereof, represented by the following formula (V),

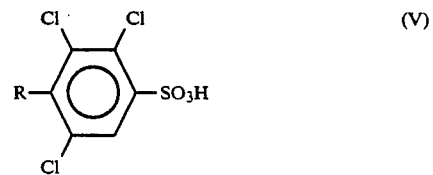

wherein R is as defined above, to hydrolysis, and subjecting the resulting hydroxy-dichlorobenzenesulfonic acid, or a salt thereof, represented by the following formula (IV),

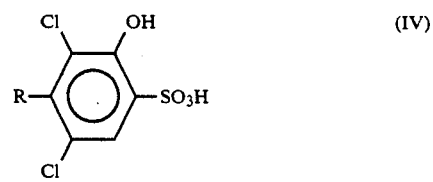

wherein R is as defined above, to nitration.

In the present invention, the trichlorobenzene (III) to be used as the starting material in the step (a) can be prepared by subjecting the trichlorobenzenesulfonic acid (V) or a salt thereof to desulfonation, and the said trichlorobenzenesulfonic acid (V) or a salt thereof to be used also as the starting material in the step (b) can be prepared by subjecting a 4-alkylbenzenesulfonic acid, or a salt thereof, represented by the following formula (VI),

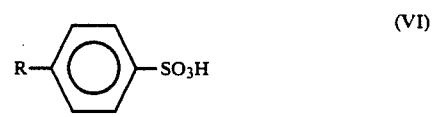

Wherein R is as defined above, to chlorination.

The present invention is explained in detail as follows.

The alkyl group represented by R in the formulas (I) to (VI) includes, for example, methyl, ethyl, n-propyl, iso-propyl, n-butyl, tert.-butyl, iso-amyl and n-octyl. The process of the present invention can be carried out most advantageously for the compounds having an ethyl or iso-propyl group as R.

The salts of the compounds represented by the formulas (IV) to (VI) include, for example, alkali metal salts, alkaline earth metal salts and amine salts. Examples thereof preferably usable are sodium, potassium and magnesium salts.

The chlorination of the 4-alkylbenzenesulfonic acid (VI) or a salt thereof to obtain the trichlorobenzenesulfonic acid (V) or a salt thereof can be carried out in a solvent in the presence or absence of a catalyst using a chlorinating agent.

The solvents usable for the chlorination includes inorganic acids, organic acids, polar organic solvents, halogenated hydrocarbons and mixtures thereof.

Examples of the inorganic acids are mineral acids such as sulfuric acid, hydrochloric acid and the like. They may be used in combination with sulfuric anhydride or chlorosulfonic acid.

Examples of the organic solvents are acetic acid, trichloroacetic acid, dichloroacetic acid, monochloroacetic acid and the like.

Examples of the polar organic solvents are nitrobenzene, N,N-dimethylformamide and the like.

Examples of the halogenated hydrocarbons are methylene chloride, chloroform, carbon tetrachloride, mono- or di-chlorobenzene and the like.

Of these solvents, preferred are inorganic solvents and halogenated hydrocarbons, and particularly preferred are inorganic solvents such as sulfuric acid.

The catalyst which may be or may not be employed for the chlorination includes, for example, iron chloride, antimony chloride, aluminum chloride, iodine and the like. Although the amount thereof is not particularly limited, preferably it ranges from 1 to 10% by weight based on the weight of the 4-alkylbenzenesulfonic acid (VI) or a salt thereof.

The chlorinating agent usable is not particularly limited, but preferably it includes chlorine gas, sulfuryl chloride and the like.

In the present invention, the chlorination reaction is continued until a content of the compound (V) or a salt thereof in the reaction mixture reaches a maximum value or nearly. More specifically, the chlorination reaction can be discontinued when the content reaches preferably 60% by weight or higher, more preferably 70 to 90% by weight based on the weight of the reaction mixture which means the sum of the starting compound (VI) or a salt thereof, if any, and the product produced by the chlorination reaction. In order to effect such chlorination reaction, the chlorinating agent can be used in an amount of 2 to 6 moles, preferably 2.5 to 4.5 moles, more preferably 2.7 to 4 moles per mole of the compound (VI) or a salt thereof, and the reaction can be carried out at a temperature of 0° to 150° C., preferably 20° to 80° C.

After the chlorination reaction is over, if necessary, the desired trichlorobenzenesulfonic acid (V) or a salt thereof can be isolated from the reaction mixture in a conventional manner.

Among the compounds (V) or salts thereof obtained in accordance with the present invention, a trichlorobenzenesulfonic acid, or a salt thereof, represented by the following formula (V'),

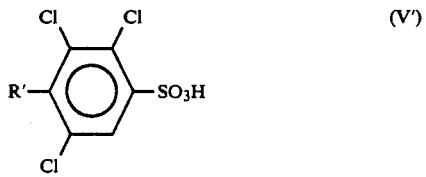

wherein R' is a straight or branched alkyl group having 2 to 8 carbon atoms, is novel.

The desulfonation of the trichlorobenzenesulfonic acid (V) or a salt thereof to obtain the trichlorobenzene (III) in the step (a) can be carried out by means of heating or steam distillation in a solvent.

When the compound (V) or a salt thereof to be used is the one produced by the chlorination of the compound (VI) as described above, the desulfonation can be carried out, if desired, after removal of the solvent used in the chlorination.

The solvent usable for the desulfonation includes mineral acids such as sulfuric acid, preferably sulfuric acid of 50 to 90% strength, more preferably 70 to 80% strength.

The temperature of desulfonation ranges usually from 140° to 220° C., preferably from 160° to 200° C.

The nitration of the trichlorobenzene (III) to obtain the nitro-trichlorobenzene (II) in the step (a) can be carried out in a manner known per se, preferably using mixed acid.

When the trichlorobenzene (III) to be used is the one produced by the desulfonation of the compound (V) or a salt thereof as described above, the trichlorobenzene produced is isolated from the reaction mixture and then used for the nitration.

Nitric acid in the mixed acid usable for the nitration can be selected from a wide range of 62 to 98% strength, and the molar ratio thereof to the compound (III) ranges from 0.95 to 1.5, preferably from 0.98 to 1.2. The sulfuric acid usable in the mixed acid may be of 62 to 98% strength. Sometimes, fuming sulfuric acid may be used. The molar ratio of sulfuric acid to the compound (III) ranges from 0.5 to 5.0, preferably 0.6 to 3.0.

The nitration reaction can be carried out usually at a temperature of 0° to 60° C., preferably at a temperature of 20° to 40° C.

After the nitration reaction is over, the nitro-trichlorobenzene (II) isolated from the reaction mixture in a conventional manner is then subjected to hydrolysis in a solvent using an alkali, thereby obtaining the desired 2,4-dichloro-3-alkyl-6-nitrophenol of the formula (I).

The solvent usable includes water, water miscible organic solvents and the like. Examples of the water miscible organic solvents are lower alcohols such as methanol, ethanol, propanol, butanol and the like, ketones, cyclic ethers and the like. Of these, lower alcohols such as methanol are preferably used.

The alkali usable includes, for example, hydroxides, oxides or carbonates of alkali metal or alkaline earth metal. Of these, sodium hydroxide and potassium hydroxide are preferably used. The alkali can be used in an amount of 2 to 10 moles, preferably 5 to 7 moles per mole of the compound (II).

The hydrolysis reaction is usually carried out under atmospheric pressure, or may be carried out under increased pressures. The reaction temperature ranges from 20° to 150° C., preferably from 40° to 100° C.

After the hydrolysis reaction is over, the reaction product can be isolated from the reaction mixture by filtration, if desired, followed by washing with water, thereby obtaining the desired compound (I). If desired, the reaction product may be subjected to neutralization using a mineral acid such as sulfuric acid.

In the present invention, the desired 2,4dichloro-3-alkyl-6-nitrophenol (I) can be produced through the step (b) as described above.

The starting trichlorobenzenesulfonic acid (V) or a salt thereof can be prepared by the chlorination of 4- alkylbenzenesulfonic acid (VI) or a salt thereof as described above.

The hydrolysis of the trichlorobenzenesulfonic acid (V) or a salt thereof can be carried out in a solvent using an alkali.

The solvent usable includes water, an organic solvent and a mixture thereof. Examples of the organic solvents are aliphatic alcohols, ketones and ethers. Of these, preferred are butanol, amyl alcohol, hexyl alcohol, heptyl alcohol, octyl alcohol, glycol, carbitol, dimethylsulfoxide, sulforane and dioxane.

The alkali usable for the hydrolysis includes hydroxides, oxides and carbonates of alkali metal or alkaline earth metal. Of these, sodium hydroxide and potassium hydroxide are preferred. The alkali can be used in an amount of 2 to 20 moles, preferably 3 to 10 moles per mole of the trichlorobenzenesulfonic acid (V) or a salt thereof.

The hydrolysis reaction can be carried out usually under atmospheric pressure, or if desired, under increased pressures. The reaction temperature ranges from 110° to 230° C., preferably from 120° to 180° C.

After the hydrolysis reaction is over, the reaction product (IV) isolated from the reaction mixture can be subjected to nitration, thereby obtaining the desired 2,4-dichloro-3-alkyl-6-nitrophenol (I).

The nitration can be carried out in any manner known per se. For example, it can be carried out using nitric acid as a nitrating agent, if desired, in sulfuric acid. In this reaction, the nitric acid is 20 to 98% strength, and is used in an amount of 1.05 to 20 moles per mole of the compound (IV) or a salt thereof. The sulfuric acid, if used, is 20 to 98% strength, and is used in an amount upto 15 times by weight of the weight of the compound (IV), or a salt thereof. The nitration reaction can be effected at a temperature of 0° to 100° C., preferably 20° to 50° C.

After the nitration reaction is over, the reaction product can be isolated from the reaction mixture by filtration, if desired, followed by washing with water, thereby obtaining the desired 2,4-dichloro-3-alkyl-6-nitrophenol (I).

In accordance with the present invention, the 2,4-dichloro-3-alkyl-6-nitrophenol can be produced industrially advantageously in a high purity using as a starting material the 4-alkylbenzenesulfonic acid (VI) or a salt thereof which is easily available.

The present invention is illustrated in more detail with reference to the following Examples, which are only illustrative, in Examples, parts and % are by weight.

EXAMPLE 1

Iodine (5 parts) was dissolved in 96% sulfuric acid (1000 parts), and 4-ethylbenzenesulfonic acid (186 parts) was added thereto. Into the mixture was introduced chlorine (about 235 parts), while being stirred at a temperature of 40° to 60° C. Then, the content of 2,3,5-trichloro-5-ethylbenzenesulfonic acid in the chlorination reaction mixture was found to be 78.8%. The reaction mixture was poured in water (2700 parts) and 28% aqueous sodium hydroxide solution (400 parts) was added thereto to precipitate crystals. The crystals were collected on a filter and then dried to obtain a white crystalline product (308 parts). The product was chromatographically analyzed (HPLC) to find 82.5% of a sodium 2,3,5-trichloro-4-ethylbenzenesulfonate content, 13.0% of a sodium 2,3,5,6-tetrachloro-4-ethylbenzenesulfonate content and 3.3% of a sodium 3,5-dichloro-4-ethylbenzenesulfonate content, and the yield of sodium 2,3,5-trichloro-4-ethylbenzenesulfonate was calculated to be 81.6%.

EXAMPLE 2

Example 1 was repeated, provided that 4-isopropylbenzenesulfonic acid (200 parts) was used in place of the 4-ethylbenzenesulfonic acid, thereby obtaining a reaction product (314 parts). The HPLC analysis found 78.3% of a sodium 2,3,5-trichloro-4-isopropylbenzenesulfonate content, 16.5% of a sodium 2,3,5,6-tetrachloro-4-isopropylbenzenesulfonate content and 4.8% of a sodium 3,5-dichloro-4-isopropylbenzenesulfonate content, and the yield was 75.5%.

EXAMPLE 3

Into 96% sulfuric acid (250 parts) were added iodine (5 parts) and sodium 4-ethylbenzenesulfonate (52 parts), and chlorine (about 60 parts) was introduced in the mixture, while being stirred at a temperature of 40° to 60° C. Then, water (500 parts) was added to the reaction mixture to precipitate crystals, which were collected on a filter and then dried to obtain a product (75.9 parts). The HPLC analysis found 82.5% of a sodium 2,3,5-trichloro-4-ethylbenzenesulfonate content, 13.0% of a sodium 2,3,5,6-tetrachloro-4-ethylbenzenesulfonate content and 3.3% of a sodium 3,5-dichloro-4-ethylbenzenesulfonate content, and the yield was 80.5%.

EXAMPLE 4

Iodine (5 parts) was dissolved in a mixed solvent of carbon tetrachloride (100 parts) and acetic acid (150 parts), and 4-ethylbenzenesulfonic acid (46.5 parts) was added thereto. Chlorine (about 60 parts) was introduced in the mixture, while being stirred at a temperature of 50° to 70° C. After the reaction was over, nitrogen was blown into the reaction mixture to remove excess chlorine, and thereafter, carbon tetrachloride was removed under reduced pressure. The resulting reaction mixture was mixed with water (150 parts) and cooled to precipitate crystals, which were collected on a filter and then dried to obtain a crude product (65 parts). The HPLC analysis found 78.3% of a 2,3,5-trichloro-4-ethylbenzenesulfonic acid content, 16.6% of a 2,3,5,6-tetrachloro-4-ethylbenzenesulfonic acid content and 1.8% of a 3,5-dichloro-4-ethylbenzenesulfonic acid content, and the yield was 70%.

EXAMPLE 5

Iodine (5 parts) was dissolved in 96% sulfuric acid (1000 parts) and 4-ethylbenzenesulfonic acid (186 parts) was added thereto. Chlorine (about 235 parts) was introduced therein, while being stirred at a temperature of 40° to 60° C. Then, a 2,3,5-trichloro-4-ethylbenzenesulfonic acid content in the reaction mixture reached 78.3%. Successively, water (200 parts) was added to the reaction mixture so as to make a ratio of sulfuric acid to water 8:2, and the reaction mixture was subjected to steam distillation at a temperature of 160° to 200° C., thereby performing desulfonation reaction. Mixed acid consisting of 67% nitric acid (110 parts) and concentrated sulfuric acid (174 parts) was added dropwise to the desulfonation reaction product isolated from water, while being stirred at a temperature of 20° to 40° C., and the mixture was kept at that temperature for 1 to 3 hours. Thereafter, the reaction mixture was poured into water (950 parts) at a temperature of 30° C. or below.

The reaction product was separated from water and then washed with water. The crude product of 2,3,5-trichloro-4-ethylnitrobenzene (220 parts) was added to a mixture of methanol (1560 parts), water (200 parts) and potassium hydroxide (240 parts), and the resulting mixture was refluxed for 4 hours. Thereafter, the reaction mixture was cooled to ambient temperature to deposit precipitate. The precipitate separated and washed with methanol and then water was placed in 20 % sulfuric acid (510 parts). The mixture was stirred for 3 hours at a temperature of 70° to 75° C., and then cooled to produce crystals of 2,4-dichloro-3-ethyl-6-nitrophenol. The crystals were collected on a filter, washed with water and then dried to obtain a desired product (141.8 parts). The over-all yield from 4-ethylbenzenesulfonic acid was found to be 60.1 %. The product had a melting point of 45.1° to 46.5° C.

Elementary analysis: Found: H: 3.03% C: 40.50% N: 5.88% Cl: 30.2% Calculated: H: 2.99% C: 40.71% N: 5.93% Cl: 30.04%

EXAMPLE 6

Example 5 was repeated, provided that 4-isopropylbenzenesulfonic acid (200 parts) was used in place of the 4-ethylbenzenesulfonic acid, thereby obtaining 2,4-dichloro-3-isopropyl-6-nitrophenol (119 parts), m.p. 35.2 to 36.7° C., in the over-all yield of 47.6%.

Example 7

Iodine (5 parts) and sodium 4-ethylbenzenesulfonate (52 parts) were added to 96% sulfuric acid (250 parts), and chlorine (about 60 parts) was introduced into the mixture, while being stirred at a temperature of 40° to 60° C. After the reaction was over, water (500 parts) was added to the reaction mixture to produce crystals. The crystals were separated by filtration and then dried to obtain sodium 2,3,5-trichloro-4-ethylbenzenesulfonate (75.9 parts) in a purity of 82.5%. The resulting sodium 2,3,5-trichloro-4-ethylbenzenesulfonate (61 parts) was added to 78% sulfuric acid (650 parts), and the mixture was subjected to steam distillation at a temperature of 150° to 200° C. using superheated steam. The oily distillate was separated from water to obtain a crude product of 2,3,6-trichloroethylbenzene (38.8 parts) in a purity of 82.5%. To the crude product (25 parts) was drowise added mixed acid of 67% nitric acid (14 parts) and concentrated sulfuric acid (22 parts), while being stirred at a temperature of 20° to 40° C., and the mixture was kept at that temperature for 1 to 3 hours. Thereafter, the reaction mixture was poured in water (125 parts) at a temperature of 30° C. or below. The reaction product was separated from water and washed with water to obtain a crude product of 2,3,5-trichloro-4-ethylnitrobenzene (27.9 parts) in a purity of 87.5%. Successively, the product (25.4 parts) was placed in a solution of methanol (180 parts), water (23 parts) and potassium hydroxide (33 parts), and the mixture was stirred under reflux for 4 hours. Thereafter, the reaction mixture was cooled to ambient temperature to produce dark red crystals. The crystals separated and washed with methanol and then water were placed in a 20% aqueous sulfuric acid solution (59 parts). The mixture was stirred at a temperature of 70° to 75° C. for 3 hours, and then cooled to produce crystalline 2,4-dichloro-3-ethyl-6-nitrophenol, which was separated by filtration, washed with water and then dried. Thus, the desired product (16.2 parts), m.p. 45.2° to 46.2° C., was obtained in the over-all yield of 58.6%.

EXAMPLE 8

Iodine (5 parts) was dissolved in a mixed solvent of carbon tetrachloride (100 parts) and acetic acid (150 parts), and 4-ethylbenzenesulfonic acid (46.5 parts) was added thereto. Chlorine (about 60 parts) was introduced into the mixture, while being stirred at a temperature of 50° to 70° C. After the chlorination reaction was over, nitrogen was blown into the reaction mixture to remove excess chlorine, and carbon tetrachloride was removed under reduced pressures. The resulting reaction mixture was mixed with water (150 parts) and cooled to produce crystals, which were collected on a filter and dried to obtain a crude product of 2,3,5-trichloro-4-ethylbenzenesulfonic acid (65 parts) in a purity of 78.3%.

The crude product was subjected to desulfonation, nitration and hydrolysis in respective manners similar to those of Example 5, thereby obtaining 2,4-dichloro3-ethyl-6-nitrophenol (30.2 parts) in the over-all yield of 51.2%.

EXAMPLE 9

Example 7 was repeated, provided that the hydrolysis reaction was carried out using sodium hydroxide (20 parts) in place of potassium hydroxide (33 parts), thereby obtaining 2,4-dichloro-3-ethyl-6-nitrophenol (13.0 parts) in the over all yield of 47.4%.

EXAMPLE 10

Potassium hydroxide (32 parts) was dissolved in ethylene glycol (200 parts), and successively the crude sodium 2,3,5-trichloro-4-ethylbenzenesulfonate (32 parts) obtained in Example 1 was added thereto. The mixture was allowed to react at a temperature of 140° to 160° C. for 12 hours. After the reaction was over, the reaction mixture was mixed with water (200 parts), and adjusted the pH within a range of 3 to 6 to produce crystals. Water containing crystals collected on a filter was placed in 25% sulfuric acid (350 parts), and 62% nitric acid (74 parts) was dropwise added thereto, while being stirred at a temperature of 25° to 50° C. The mixture was stirred at that temperature for 1 hour, and thereafter cooled to 5° C. to produce crystals, which were collected on a filter, washed with water and then dried to obtain 2,4-dichloro-3-ethyl-6-nitrophenol (15.6 parts) having a melting point of 46.2° to 47.2° C. in a yield of 78.1%.

Elementary analysis: Found: C: 40.49% H: 3.04% N: 5.83% Cl: 29.8% Calculated: C: 40.71% H: 2.99% N: 5.93% Cl: 30.04%

EXAMPLES 11 to 14

Example 10 was repeated, provided that each reaction was carried out under reaction conditions as shown in the following table, thereby obtaining the results also as shown therein.

TABLE

| Example No. | Reaction solvent | Reaction temperature (°C.) | Reaction time (hr) | Amount of 62% nitric acid (parts) | Results (yield %) |
| --- | --- | --- | --- | --- | --- |
| 11 | Sulforane | 170–180 | 7.0 | 80 | 70.3 |

TABLE-continued

| Example No. | Reaction solvent | Reaction temperature (°C.) | Reaction time (hr) | Amount of 62% nitric acid (parts) | Results (yield %) |
|---|---|---|---|---|---|
| 12 | Octyl alcohol | 180–190 | 15.0 | 52 | 43.1 |
| 13 | Diethylene glycol | 160–170 | 10.0 | 72 | 68.2 |
| 14 | Carbitol | 150–160 | 10.0 | 80 | 73.2 |

EXAMPLE 15

Example 10 was repeated, provided that the hydrolysis reaction was carried out using sodium hydroxide (24 parts) in place of potassium hydroxide (32 parts), thereby obtaining 2,4-dichloro-3-ethyl-6-nitrophenol (12.6 parts) in a yield of 63.1%.

EXAMPLE 16

Example 10 was repeated, provided that the crude sodium 2,3,5-trichloro-4-isopropylbenzenesulfonate (35 parts) obtained in Example 2 was used in place of the sodium 2,3,5-trichloro-4-ethylbenzenesulfonate (32 parts), thereby obtaining 2,4-dichloro-3-isopropyl-6-nitrophenol (11.4 parts) having a melting point of 35.2° to 36.7° C. in a yield of 53.8%.

Elementary analysis: Found: C: 43.40% H: 3.71% N: 5.57% Cl: 28.2% Calculated: C: 43.23% H: 3.66% N: 5.60% Cl: 28.35%

What is claimed is:

1. A process for producing a 2,4-dichloro-3-alkyl-6-nitrophenol represented by the following formula (I),

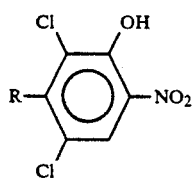 (I)

wherein R is a straight or branched alkyl group having 1 to 8 carbon atoms, which comprises (a) steps of nitrating a trichlorobenzene represented by the following formula (III),

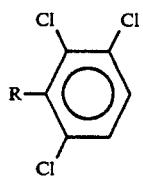 (III)

wherein R is as defined above, with mixed acid at a temperature of 0° to 60° C. to obtain a nitro-trichlorobenzene represented by the following formula (II),

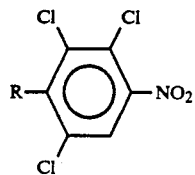 (II)

wherein R is as defined above, and hydrolyzing the nitrotrichlorobenzene of the formula (II) in a solvent using an alkali at a temperature of 20° to 150° C., or (b) steps of hydrolyzing a trichlorobenzenesulfonic acid, represented by the following formula (V),

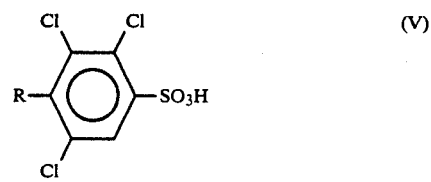 (V)

wherein R is as defined above, or a salt thereof, in a solvent using an alkali at a temperature of 110° to 130° C. to obtain a hydroxydichlorobenzenesulfonic acid represented by the following formula (IV),

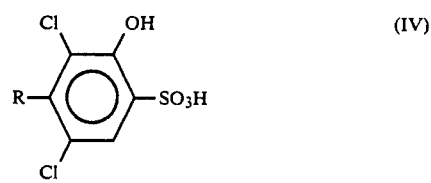 (IV)

wherein R is as defined above, or a salt thereof, and nitrating the hydroxy-dichlorobenzene sulfonic acid of the formula (IV), or a salt thereof, with nitric acid at a temperature of 0° to 100° C.

2. A process for producing a 2,4-dichloro-3-alkyl-6-nitrophenol represented by the following formula (I),

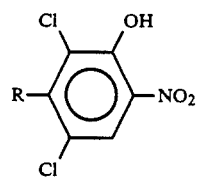 (I)

wherein R is a straight or branched alkyl group having 1 to 8 carbon atoms, which comprises desulfonating a trichlorobenzenesulfonic acid represented by the following formula (V),

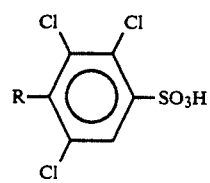 (V)

wherein R is as defined above, or a salt thereof, in a solvent at a temperature of 140° to 220° C. to obtain a trichlorobenzene represented by the following formula (II),

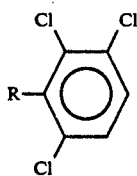 (III)

wherein R is as defined above, nitrating the trichlorobenzene of the formula (III) with mixed acid at a temperature of 0° to 60° C. to obtain a nitro-trichlorobenzene represented by the following formula (II),

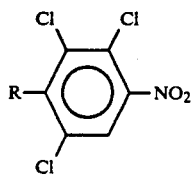 (II)

wherein R is as defined above, and hydrolyzing the nitrotrichlorobenzene of the formula (II) in a solvent using an alkali at a temperature of 20° to 150° C.

3. A process for producing 2,4-dichloro-3-alkyl-6-nitrophenol represented by the following formula (I),

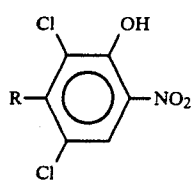 (I)

wherein R is a straight or branched alkyl group having 1 to 8 carbon atoms, which comprises chlorinating a 4-alkylbenzenesulfonic acid represented by the following formula (VI),

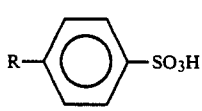 (VI)

wherein R is as defined above, or a salt thereof, in a solvent in the presence or absence of a catalyst using a chlorinating agent at a temperature of 0° to 150° C. to obtain a trichlorobenzenesulfonic acid represented by the following formula (V),

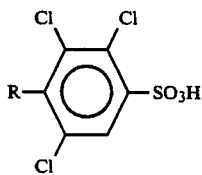 (V)

wherein R is as defined above, or a salt thereof, desulfonating the trichlorobenzene sulfonic acid, or a salt thereof, in a solvent at a temperature of 140° to 220° C. to obtain a trichlorobenzene represented by the following formula (III),

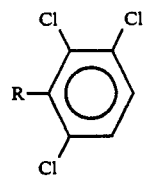 (III)

wherein R is as defined above, nitrating the trichlorobenzene of the formula (III) which mixed acid at a temperature of 0° to 60° C. to obtain a nitro-trichlorobenzene represented by the following formula (II),

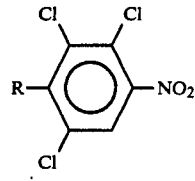 (II)

wherein R is as defined above, and hydrolyzing the nitrotrichlorobenzene of the formula (II) in a solvent using an alkali at a temperature of 20° to 150° C.

4. A process for producing a 2,4-dichloro-3-alkyl-6-nitrophenol represented by the following formula (I),

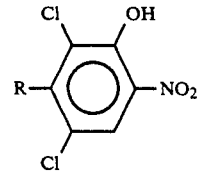 (I)

wherein R is a straight or branched alkyl group having 1 to 8 carbon atoms, which comprises chlorinating a 4-alkylebenzenesulfonic acid represented by the following formula (VI),

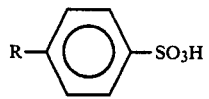 (VI)

wherein R is as defined above, or a salt thereof, in a solvent in the presence or absence of a catalyst using a chlorinating agent at a temperature of 0° to 150° C., to obtain a trichlorobenzenesulfonic acid represented by the following formula (V),

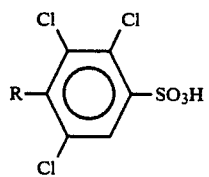 (V)

wherein R is as defined above, or a salt thereof, hydrolyzing the trichlorobenzenesulfonic acid of the formula (V), or a salt thereof, in a solvent using an alkali at a temperature of 110° to 130° C. to obtain a hydroxydichlorobenzenesulfonic acid represented by the following formula (IV),

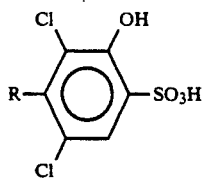 (IV)

wherein R is as defined above, or a salt thereof, and nitrating the hydroxy-dichlorobenzenesulfonic acid of the formula (IV), or a slat thereof, with nitric acid at a temperature of 0° to 100° C.

5. A process according to claim 1, wherein molar ratio of nitric acid and sulfuric acid in the mixed acid to the trichlorobenzene represented by the formula (III) is 0.95 to 1.5 and 0.5 to 5.0, respectively.

6. A process according to claim 1, wherein in (a) during the hydrolysis, the alkali is used in an amount of 2 to 10 moles per mole of the nitrotrichlorobenzene represented by the formula (II).

7. A process according to claim 1, wherein in (b), in the hydrolysis of the trichlorobenzenesulfonic acid, the alkali is used in an amount of 2 to 20 moles per mole of the trichlorobenzenesulfonic acid, or a salt thereof, represented by the formula (V).

8. A process according to claim 1, wherein in (b), the nitric acid is used in an amount of 1.05 to 20 moles per mole of the hydroxydichlorobenzenesulfonic acid, or a salt thereof, represented by the formula (IV).

9. A process according to claim 3 or 4, wherein the chlorinating agent is used in an amount of 2 to 6 moles per mole of the 4-alkylbenzenesulfonic acid or a salt thereof.

10. A process according to claim 9, wherein the chlorination is continued until a content of the trichlorobenzenesulfonic acid, or a slat thereof, represented by the formula (V) in the reaction mixture reaches 60% by weight or higher.

* * * * *